United States Patent [19]

Lang et al.

[11] Patent Number: 5,624,811
[45] Date of Patent: Apr. 29, 1997

[54] BILIRUBIN OXIDASE FROM ALFALFA AND USE OF THE ENZYME

[75] Inventors: Gunter Lang, Tutzing; Ingo Bohn, Birkenau; Hans-Willi Krell, Penzberg, all of Germany

[73] Assignee: Boehringer Mannheim GmbH, Mannheim, Germany

[21] Appl. No.: 210,371

[22] Filed: Mar. 18, 1994

[30] Foreign Application Priority Data

Mar. 24, 1993 [DE] Germany ............ 43 09 111.3

[51] Int. Cl.[6] ............ C12Q 1/26; C07K 1/00
[52] U.S. Cl. ............ 435/25; 435/4; 435/189; 436/63; 436/97; 436/811; 530/412; 530/413; 530/417; 530/418; 530/427
[58] Field of Search ............ 435/25, 4, 189; 436/63, 97, 811; 530/412, 413, 417, 418, 427; 424/94.4

[56] References Cited

U.S. PATENT DOCUMENTS

| | | | |
|---|---|---|---|
| 4,569,912 | 2/1986 | Matsui et al. | 435/189 |
| 4,677,062 | 6/1987 | Uwajima et al. | 435/189 |
| 4,701,411 | 10/1987 | Wu | 435/25 |
| 4,770,997 | 9/1988 | Yoshino et al. | 435/25 |
| 4,839,279 | 6/1989 | Kosaka et al. | 435/25 |

FOREIGN PATENT DOCUMENTS

| | | |
|---|---|---|
| 005637 | 11/1979 | European Pat. Off. . |
| 140004 | 5/1985 | European Pat. Off. . |
| 247846 | 12/1987 | European Pat. Off. . |
| 320095 | 6/1989 | European Pat. Off. . |
| 3239236 | 9/1983 | Germany . |

OTHER PUBLICATIONS

Koikeda et al., *The Journal of Biological Chemistry*, vol. 268, No. 25, Sep. 5, 1993, pp. 18801–18809.

Murao et al, *Agric. Biol. Chem.*, vol. 45, No. 10, pp. 2383–2384, 1981.

*Primary Examiner*—Michael G. Wityshyn
*Assistant Examiner*—Abdel A. Mohamed
*Attorney, Agent, or Firm*—Felfe & Lynch

[57] ABSTRACT

Enzyme specific for bilirubin which has a phenol oxidase activity of less than 0.5% and an activity for biliverdin of less than 10%, a broad pH optimum as well as a good thermostability. The enzyme is obtainable from plants such as alfalfa and is suitable for the determination as well as for the degradation of bilirubin in particular in biological liquids.

8 Claims, 2 Drawing Sheets

BILIRUBIN OXIDASE FROM ALFALFA AND USE OF THE ENZYME

BACKGROUND OF THE INVENTION

The invention concerns a bilirubin oxidase (E.C.1.3.3.5) from plants, in particular from the genus Alfalfa, a process for the isolation as well as the use of the enzyme for the determination of bilirubin or the removal of bilirubin in aqueous liquids, in particular biological liquids.

A number of enzymes with bilirubin oxidase activity from various plant sources are known. Such bilirubin-specific enzymes are isolated in particular from strains of the genus Bacillus (U.S. Pat. No. 4,770,997), Myrothecium and Coprinus (DE 32 39 236), Solanaceae, Musaceae and Liliaceae (EP 0 140 004), Compositae (EP 0 247 846) and from fungi (EP 0 005 637) and citrus fruits (EP 0 320 095). However, the bilirubin-specific enzymes isolated from the aforementioned plant genera characteristically have a relatively low specificity for bilirubin and have various side activities. The latter are a particular hindrance in diagnostic analytical methods in which a number of other components, some of which are similar to bilirubin, can be present as a result of individual differences in the composition of the respective biological sample such as blood, urine or serum. This can in addition be caused by the degradation of certain pharmaceutical agents. In the case of most known enzymes with bilirubin oxidase activity such interferences occur in particular when phenolic compounds such as catechol, hydroquinone or phenol itself are present. This non-specificity of the enzymes, i.e. an undesired phenol oxidase activity, leads to delayed reactions in the corresponding determinations and the enzymes are therefore not suitable for an application in colorimetric tests or only to a limited extent.

Other known bilirubin oxidases have a low specific activity or a high Michaelis constant for bilirubin so that interferences can occur due to the large amount of protein or enzyme which has to be added to the test in such cases.

In addition the stability at higher temperatures is not adequate in the case of a number of the previously available bilirubin oxidases. In the corresponding determinations this causes a non-linear time course of the kinetics.

The objects of the invention are therefore to provide an enzyme with bilirubin oxidase activity which has a high specificity for bilirubin and does not have any interfering contaminating activities and at the same time posesses a high thermostability and can be isolated in adequate amounts from a readily available source of raw material.

THE INVENTION

Figure 1:
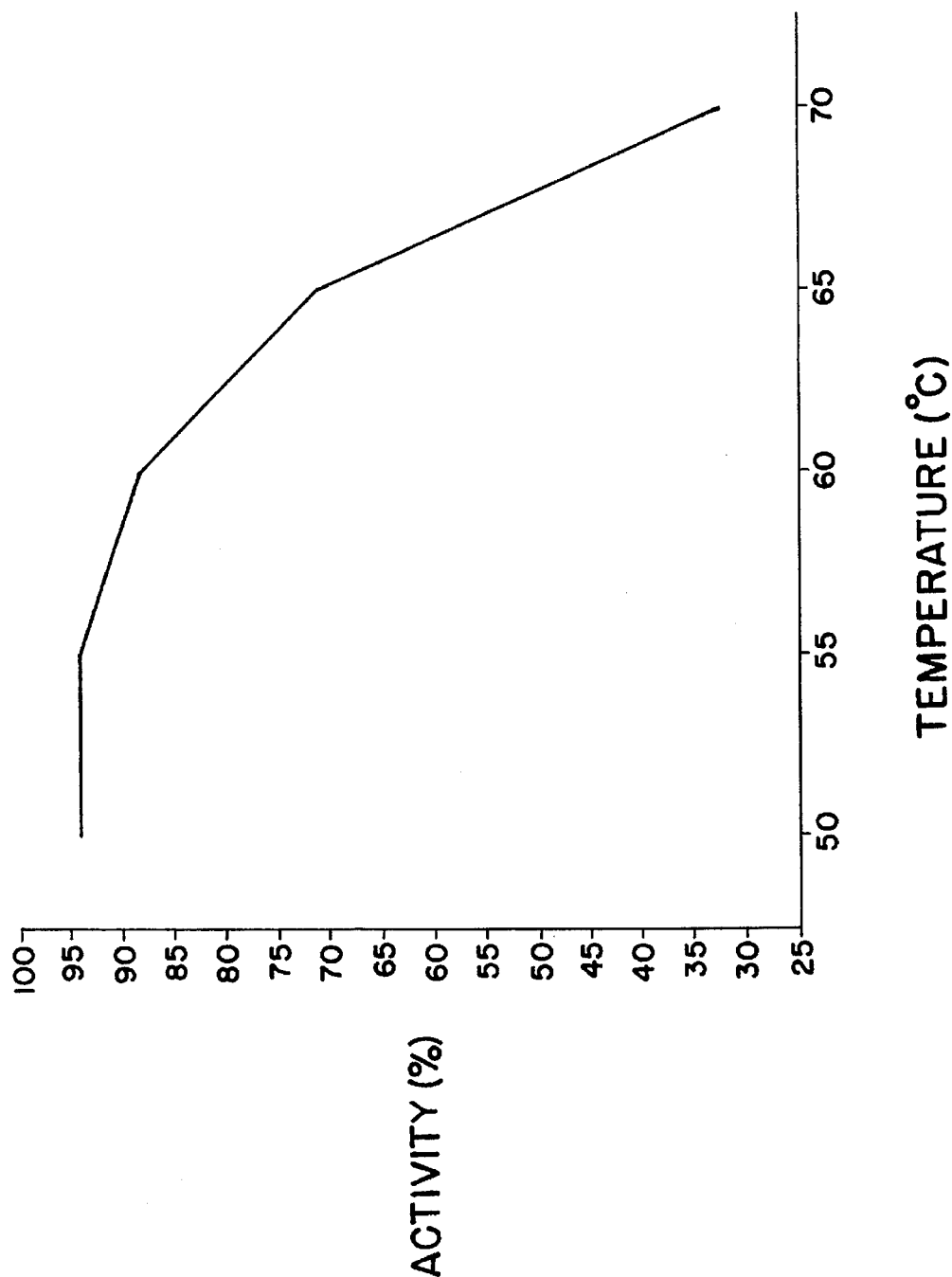
FIG. 1 shows the enzymatic activity of the bilirubin oxidase according to the invention up to a temperature of 70° C. (buffer: 50 mM citrate/NaOH, pH 4.0, 2 mM MgCl$_2$, 5 mM DTE); time: 10 minutes.
Figure 2:
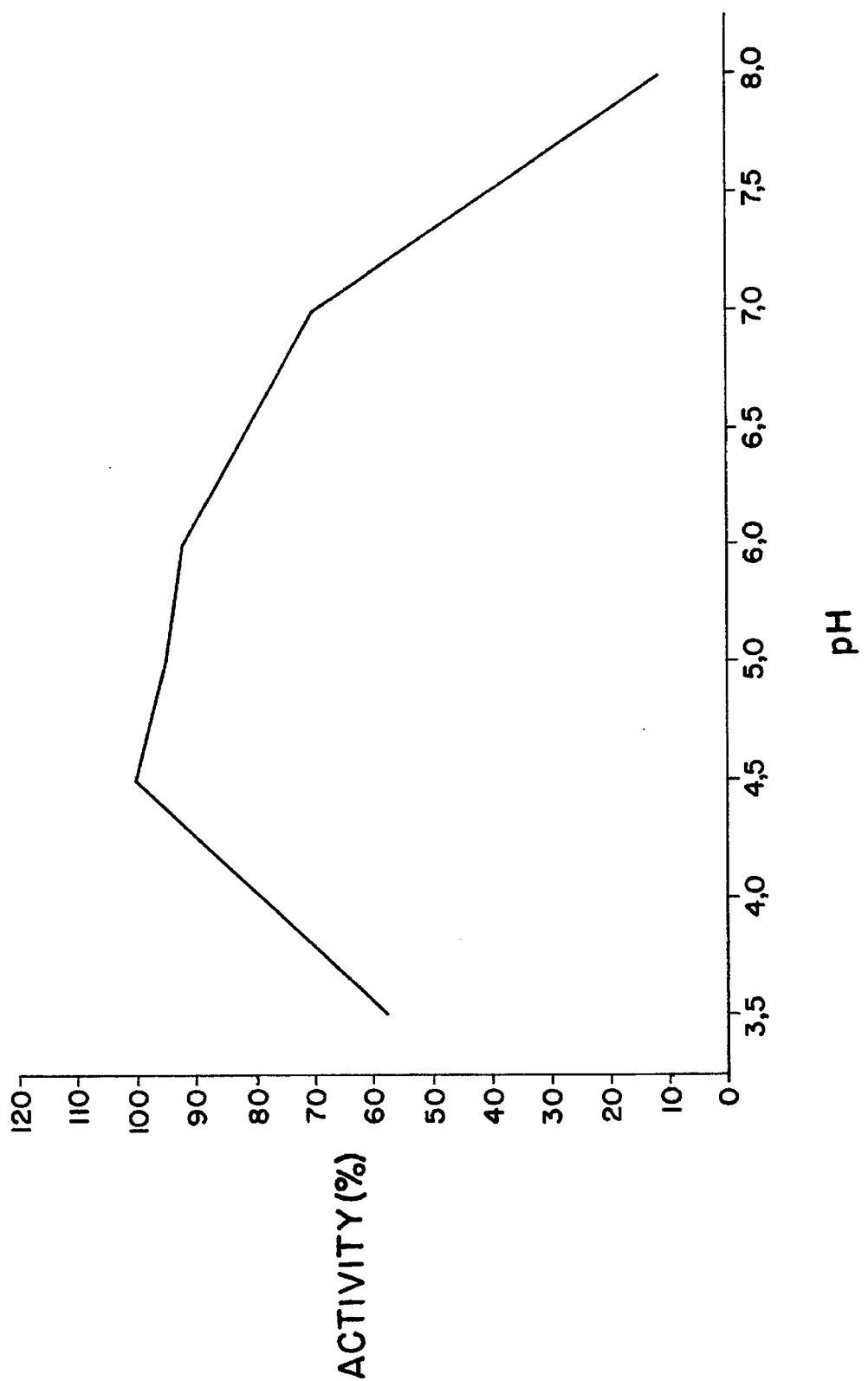
FIG. 2 shows the enzymatic activity of alfalfa bil-OD in a pH range of 3.5 and 8.0 (buffer: 50 mM citrate, pH 3.5–6.0; 50 mM TRA, pH 6.5–8.5); time: 3 hours at 25° C.

The above stated objects are is achieved by a specific enzyme for bilirubin which is distinguished by less than 0.5%, preferably less than 0.06% phenol oxidase activity, less than 10% biliverdin activity and by a good thermostability and is obtainable from a plant of the alfalfa species and in particular from its seedlings.

Since the dehydration product biliverdin and water are formed from bilirubin during the reaction in the presence of oxygen, the enzyme therefore has bilirubin oxidase activity. The bilirubin oxidase from alfalfa seedlings has no siginificant side activities. Thus a phenol oxidase activity is not detectable or it is below the detection limit which approximately corresponds to a content of 0 to 0.5%, preferably of about 0 to 0.06%. A maximum of 10% of the enzymatic activity of bilirubin oxidase from alfalfa can be attributed to the conversion of biliverdin. However, the majority of the enzyme preparations isolated from alfalfa only convert biliverdin by less than 5%.

The alfalfa enzyme with bilirubin oxidase activity can be used in a wide temperature range and namely from approximately 20° to a maximum of 70° C. The enzyme is preferably used in a temperature range of 20° to 60° C. and especially preferably of 20° to 40° C. Moreover the enzyme in contrast to most known bilirubin oxidases can be classified as thermostable. Thus the bilirubin oxidase from alfalfa still has approximately its complete initial activity after about 10 minutes at 55° C., at least 70% of this activity after about 10 minutes at 65° C. and ca. 50% at 67° C. (10 minutes).

The specific enzyme for bilirubin from alfalfa has a good activity at a pH value of approximately 3.5 to 10 The enzyme is preferably used in the pH range of 4.0 to 7.0 which has proven to be optimal and especially preferably at a pH value of about 6.0. On longer incubation (ca. 3 hours, 25° C.) the optimal pH value is between 4.0 and 6.0, preferably at pH 4.5.

The bilirubin oxidase from alfalfa has a particular specificity for bilirubin. Thus the Michaelis constant for bilirubin at ca. 25° C. is $8.0 \times 10^{-6}$ mol/l or less at a pH value of about 8.0 (TRIS/HCl buffer).

In addition the purified enzyme is characterized by a molecular weight of approximately 42000 Daltons under reducing conditions in electrophoresis (SDS-PAGE). However, a variation of approximately ±5000 Daltons has to be accepted. Furthermore, the enzyme from alfalfa has a carbohydrate content of about 7.5% and has an isoelectric point between pH 8 and 9. The enzyme is probably not a metalloprotein since the metals copper, calcium, iron and zinc could not be detected in the protein.

The alfalfa enzyme is activated by SH reagents such as dithiothreitol and/or mercaptoethanol. Sodium cholate and/or structurally related compounds have for example an inhibitory effect on the enzyme.

The bil-OD gene which codes for the bilirubin oxidase according to the invention can be cloned by means of methods familiar to a person skilled in the art and subsequently overexpressed in microorganisms and/or animal cell lines and/or plant cell lines and/or transgenic plants.

The bil-OD gene according to the invention can for example be isolated by means of specific degenerate oligonucleotide probes that are derived from the bil-OD amino acid sequence (or partial sequences) by hybridization from a suitable cDNA gene pool (e.g. cDNA gene pool from lucerne seedlings) and/or chromosomal DNA (e.g. from lucerne seedlings).

The bil-OD amino acid sequence or suitable bil-OD amino acid partial sequences can be determined by N-terminal protein sequencing of purified bil-OD or of other purified bil-OD protein fragments (e.g. after cleaving with a restriction protease such as e.g. trypsin).

The bil-OD gene according to the invention can be unequivocally identified after DNA sequencing and translation of the genetic information into the amino acid sequence by comparison with the bil-OD amino acid sequence or amino acid partial sequences determined by protein sequencing.

After cloning, the bil-OD gene can be overexpressed by means of known prokaryotic and/or eukaryotic host/vector systems (in bacteria such as e.g. Escherichia, Bacillus, Pseudomonas, and Streptomyces and/or yeasts such as e.g. Saccharomyces, Kluyveromyces, Pichia, Hansenula, Schwanniomyces and Schizosaccharomyces and/or fungi such as e.g. Aspergillus, Trichoderma and Penicillium and/or animal cell lines such as e.g. CHO and COS cells and/or transgenic plants such as e.g. tomatoes, tabacco, maize, Arabidopsis and petunias and/or viruses such as e.g. the baculo and vaccinia virus).

The invention in addition concerns a process for the isolation of bilirubin oxidase from plants of the alfalfa species. Seedlings of alfalfa (snail lucerne, Medicago sativa) are particularly suitable as a raw material. Surprisingly this raw material is characterized by a high activity of bilirubin oxidase and is widespread and available at a low cost so that the desired enzyme can be provided in a large amount and high purity. Moreover, in contrast to nicrobial raw materials, time-consuming culture procedures requiring a great deal of material are not necessary. Seeds of alfalfa can be obtained commercially from relevant suppliers such as health-food shops. In this connection the alfalfa seedlings of snail lucerne have proven to be particularly advantageous.

In order to isolate the enzyme from alfalfa, the cells of the seedlings are first disrupted in the usual manner. The crude extract is initially purified at approximately pH 5.0 by fractional precipitation i.e. with a polymeric amine (Polymin P) and ammonium sulfate —and if desired subsequent dialysis and a heat step. In this case it has proven to be particularly suitable to heat the dialysed fraction to approximately 40° to 60° C. at about pH 4.0 for ca. 10 minutes. A temperature of about 50° C. is particularly preferable for this.

The pre-purified enzyme is subsequently purified by acetone precipitation and further chromatographic steps. In this case hydrophobic chromatography and/or an affinity chromatography after a further acetone precipitation step with subsequent dialysis have proven to be particularly suitable. The hydrophobic chromatography is preferably carried out with octyl-Sepharose or phenyl-Sepharose as the column material and a dilute ammonium sulfate solution as the eluting agent. The solution preferably has an ammonium sulfate content between 0.1 and 1.5 M, particularly preferably between 0.6 and 1.0 M and the elution is carried out with decreasing concentrations of ammonium sulfate. The affinity chromatography is preferably carried out on concanavalin A-Sepharose. A solution buffered to about pH 5.0, which if desired contains stabilizers, is used for the equilibration and elution. A 10 to 100 mM citrate/sodium hydroxide buffer pH 5.0 to which a SH reagent such as dithiothreitol or mercaptoethanol and magnesium chloride have been added in millimolar concentrations has proven to be advantageous; a 50 mM citrate buffer is preferably used. In addition 5% (w/v) α-methyl-D-mannoside is added to the elution solution.

The combined eluates of the subsequent affinity chromatography can contain up to 4 KU bilirubin oxidase depending on the initial amount and quality of the seedlings, which can lead to a specific activity of the purified enzyme of up to 100 U/mg or more. In most cases an enzyme fraction with a specific activity of 80 U/mg or more is obtained using the process according to the invention.

The new bilirubin oxidase purified in this manner which has particularly low side activities and an improved substrate specificity is suitable for the qualitative determination and especially well-suited for the quantitative determination of bilirubin in aqueous liquids. The biologica liquids can be whole blood, plasma, serum, and urine samples. However, the determinations of bilirubin can be in other liquids based on human or animal tissues or secretions.

Bilirubin analyses in colorimetric tests that are free from interference result from the fact that the enzyme is practically free phenol oxidase activity (below the detection limit) Bilirubin has a characteristic absorbance peak at 440 nanometers (nm) of the electromagnetic spectrum.

Consequently the amount of bilirubin cleaved by the enzyme (measured at a wavelength of 440 nm) is inversely proportional to the measured absorbance. This is as familiar to a person skilled in the art as the basic procedure for the enzymatic determination of bilirubin (EP 0 238 914, EP 0 247 846, Agric. Biol. Chem. 45, 2383–2384 (1981) inter alia). In this process the sample liquid is usually brought into contact with the enzyme specific for bilirubin in order to bring about a reaction of bilirubin with the enzyme while producing a determinable change and the generated change is determined sequentially or afterwards. The enzyme according to the invention is preferably used in a concentration range of 0.005 to 20 U/ml, particularly preferably at a concentration of about 0.05 to 5 U/ml. As a rule all substances which buffer between pH 7 and pH 9 and preferably at about pH 8.0 at a concentration of 20 to 250 mM are suitable as a buffer for the determination. A 50 mM TRI/HC1 or TRA buffer pH 8.0 has proven to be particularly advantageous (TRI=Tris (hydroxy-methyl)-amino-methane; TRA=triethanolamine). The temperature for the determination is usually between 20° and 40° C., temperatures of up to 65° C. have also proven to be usable in this case.

The enzyme according to the invention is also suitable for removing bilirubin from aqueous and in particular biological liquids. This can for example be achieved by passing the respective biological sample through a filter device containing the enzyme. Such filter devices can be used for the complete removal of bilirubin and its degradation products when combined with other adsorption agents or procedures. This can for example be carried out ex vivo for human whole blood after which the purified blood is either returned to the corresponding person or is stored or used as conserved blood.

In order to degrade or quantitatively remove bilirubin the enzyme according to the invention is added in a concentration range of 0.5 to 20 U/ml after an appropriate initial test with regard to the content of bilirubin present. All other parameters can be selected as stated above.

In addition the enzyme according to the invention can be used in analytical tests or methods in which analytes that are different from bilirubin are determined for example in order to exclude or reduce interferences due to endogenous bilirubin in the sample or bilirubin which is present for other reasons.

The aqueous sample which contains the analyte/analytes which are different from bilirubin as well as bilirubin as an interfering component is accordingly brought into contact with a reactive composition for the analyte thereby generating a determinable change. The enzyme according to the invention is added to the sample either before or during the contacting in order to degrade bilirubin and reduce its interfering potential during the generation of the determinable change. The determinable change is determined continuously or after a certain time interval. An addition of 0.05 to 5.0 U/ml alfalfa bilirubin oxidase has proven to be particularly advantageous for such measures to reduce interferences. However, the required amount of bilirubin oxidase can vary within wide limits depending on the sample and the analytical system.

The enzyme according to the invention can be used in a wide temperature and pH range for the determination as well as for the removal of bilirubin. Thus the enzyme can be used at temperatures of approximately 20° to 70° C. and in a pH range of 3.5 to 10. However, a range of 20° to 40° C. and a pH of 4.0 to 8.5 is preferably selected. The enzyme has a broad pH optimum of pH 4.5 to 8.0, the temperature optimum is at about 25° C. (TRIS/HCl buffer).

It is intended to elucidate the invention in more detail by the following examples without limiting it thereby.

EXAMPLE 1

Isolation of bilirubin oxidase
Raw material:
  alfalfa seedlings (snail lucerne);
  health-food shops (Battenberg Company, Dießen)
Extraction:
  Extraction buffer:
  30 mM citrate/NaOH pH 5.0
  1 mM dithiothreitol (DTE)
  1 mM $MgCl_2$ 4 l ice-cold extraction buffer is added to 4 kg alfalfa seedlings (fresh or frozen). The homogenized seedlings are pressed out with nylon gauze, 4 l of the buffer is added to the residue, it is again homogenized and pressed and both extracts are combined.

Polymin P separation:
  dialysis buffer:
  50 mM citrate/NaOH pH 5.0
  1 mM DTE
  1 mM $MgCl_2$ After a preliminary test the supernatant is admixed with ca. 1% of a 10% Polymn P solution, pH 7. The precipitated precipitate is centrifuged.

The extracts are precipitated at pH 5.0 (pH monitoring) with solid ammonium sulfate up to a concentration of 3.2 M, stirred for ca. 1 hour and then centrifuged (10,000×g) for ca. 50 minutes. The supernatant is discarded.

The ammonium sulfate (AS) precipitate is taken up as concentrated as possible in dialysis buffer.

Dialysis

The suspended AS precipitate is dialysed against 3×10 l dialysis buffer. The dialysate is subsequently centrifuged to form a clear solution (conductivity=8.5 µS).

Heating

The dialysate is adjusted to pH 4.0 and heated to 50° C. for ca. 10 minutes in a water bath. Subsequently it is cooled to ca. 5° C. in an ice bath. The sedimented precipitate is centrifuged at ca. 10,000× g for 20 minutes and subsequently the pH value is reset to pH 5.0 using 2N sodium hyroxide solution.

Acetone precipitation

The cooled enzyme solution is admixed with 2 volumes of deep-cooled acetone. It is subsequently stirred for ca. 10,000× g for 20 minutes.

The precipitate is taken up in a concentrated form in dialysis buffer and centrifuged to form a clear solution.

Octyl-Sepharose chromatography

A chromatography column of appropriated size (capacity: ca. 100 U/mg) is equilibrated with dialysis buffer and 1M AS.

The extract of the acetone precipitation is adjusted to 1M AS applied to the prepared column.

Washing:
  Dialysis buffer+1M AS 1 column volume

Elution:
  Dialysis buffer +0.6M AS 2 column volumes
  The bilirubin oxidase elutes at 0.6 M AS.
  Yield: Usable fractions contain 40–60% of the activity.

Dialysis

The combined fractions are dialysed overnight against dialysis buffer to remove the remaining ammonium sulfate.

Acetone precipitation 2 volumes acetone (deep-cooled) is added to the dialysed fractions at ca. +4° C. After ca. 15 minutes stirring, it is centrifuged for 20 minutes at ca. 10 000× x g. The precipitate is taken up as concentrated as possible in dialysis buffer and if desired is centrifuged to form a clear solution.

Concanavalin A-Sepharose chromatography

The enzyme solution is applied to a con A-Sepharose column equilibrated with dialysis buffer.

It is subsequently washed with approximately 5 column volumes of dialysis buffer.

The elution is carried out with 3 column volumes of dialysis buffer containing 5% α-methyl-D-mannoside.

The active eluates are pooled.

Table 1 shows the data for the concentration of the enzyme after the individual steps of the procedure:

TABLE 1

Bilirubin oxidase concentration from 4 kg alfalfa seedlings

| Step | Volume [ml] | Units [KU] | protein [g] | spec. act. [U/mg] | Yield [%] |
| --- | --- | --- | --- | --- | --- |
| Extraction | 4000 | 15 | 4.54 | 3.3 | 100 |
| Polymin P fraction | 4000 | 15 | 4.54 | 3.3 | 100 |
| heating | 200 | 15 | 1.87 | 8.0 | 100 |
| acetone fraction | 50 | 6.4 | 0.42 | 15.0 | 42 |
| octyl-Sepharose | 10 | 3.8 | 0.118 | 32 | 25 |
| acetone precipitation + con A-Sepharose | 2.5 | 2 | 0.025 | 80 | 13 |

EXAMPLE 2

Determination of bilirubin

Reaction scheme: bilirubin + 1/2 $O_2$ 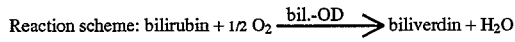 biliverdin + $H_2O$

Solutions: 1. TRIS/HCl buffer:

(50 mmol/l; pH 8.0):
    788 mg Tris hydrochloride is dissolved in 80 ml water (redistilled), adjusted to pH 8.0 with 2N NaOH and made up to 100 ml.
  2. Bilirubin oxidase solution:
    3 U/ml bilirubin oxidase (final concentration) is dissolved in TRIS/HCl buffer.

Procedure:
The decrease in absorbance at 440 nm is measured.

| Measurement radiation: 440 nm | Light path: 1.0 cm |
|---|---|
| Test volume: 3.3 ml | Measurement temperature 25° C. |
| pipette into cuvette | |
| Tris buffer (1) | 2.0 ml |
| bilirubin oxidase solution (2) | 1.0 ml |
| mix, incubate, add | 0.1 ml |
| bilirubin sample | |

The absorbance is determined after 30 minutes.
Calculation:

$$A \times \frac{3.1}{42 \cdot 1 \cdot v} = \text{U/ml sample solution.}$$

We claim:

1. A process for the isolation of an enzyme specific for bilirubin from at least one plant of the alfalfa species, comprising: obtaining a crude extract from the alfalfa; subjecting the crude extract to a fractional precipitation to obtain a precipitate; heating the precipitate; and subjecting the precipitate to at least one chromatographic separation.

2. A process for obtaining bilirubin oxidase from alfalfa comprising:

(a) homogenizing a sample of alfalfa to form an extract;

(b) fractionally precipitating said extract to form a precipitate and a dialysate;

(c) heating the dialysate; and chromatographically separating the heated dialysate at least twice to obtain the bilirubin oxidase.

3. The process of claim 2 wherein the fractional precipitation comprises contacting said extract (1) with a polymeric amine and (2) with ammonium sulfate solution.

4. The process of claim 2 wherein the heating is carried out for 10 minutes at 40° to 60° C. at a pH of about 4.0.

5. The process of claim 2 wherein an acetone precipitation is carried out before each of the chromatographic separation steps.

6. The process of claim 2 wherein a dialysis is carried out before each of the chromatographic separation steps.

7. The process of claim 2 wherein at least one chromatographic separation is by hydrophobic chromatography or an affinity chromatography.

8. The process of claim 2 wherein at least one chromatographic separation is on an octyl-Sepharose or concanavalin A-Sepharose column.

* * * * *